United States Patent
Zeidler et al.

(10) Patent No.: US 6,322,816 B1
(45) Date of Patent: Nov. 27, 2001

(54) FAST-ACTING ANALGESIC

(75) Inventors: Jürgen Zeidler, Mutterstadt; Jörg Neumann, Limburgerhof; Bernd Leipold, Mannheim; Jörg Rosenberg, Ellerstadt; Gunther Berndl, Herxheim; Jörg Breitenbach, Mannheim; Christiane Vollgraf, Bobenheim-Roxheim, all of (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/463,849

(22) PCT Filed: Jul. 21, 1998

(86) PCT No.: PCT/EP98/04552

§ 371 Date: Feb. 1, 2000

§ 102(e) Date: Feb. 1, 2000

(87) PCT Pub. No.: WO99/06038

PCT Pub. Date: Feb. 11, 1999

(30) Foreign Application Priority Data

Aug. 1, 1997 (DE) ................................. 197 33 505

(51) Int. Cl.[7] ............... A61K 9/14; A61K 9/28; A61K 9/26; A61K 9/24
(52) U.S. Cl. ............ 424/486; 424/474; 424/470; 424/473
(58) Field of Search ............... 424/451, 464, 424/486; 525/326

(56) References Cited

U.S. PATENT DOCUMENTS

| | | | |
|---|---|---|---|
| 4,704,436 | * 11/1987 | Barabas | 525/326 |
| 4,877,620 | 10/1989 | Loew et al. | 424/451 |
| 5,560,924 | * 10/1996 | Wunderlich et al. | 424/451 |
| 5,741,519 | * 4/1998 | Rosenberg et al. | 424/464 |

FOREIGN PATENT DOCUMENTS

| | | |
|---|---|---|
| 36 39 038 | 7/1986 | (DE) . |
| 41 40 185 | 8/1993 | (DE) . |
| 196 35 676 | 3/1998 | (DE) . |
| 96/14058 | 5/1996 | (WO) . |
| 9614058 | * 5/1996 | (WO) . |
| 96/29061 | 9/1996 | (WO) . |
| 9726866 | * 7/1997 | (WO) . |
| 97/26866 | 7/1997 | (WO) . |

OTHER PUBLICATIONS

BASF Patent Appl. OZ 0050/46534=USSN 09/101,694 DataBase Abstr. XP002085752.

* cited by examiner

Primary Examiner—Thurman K. Page
Assistant Examiner—Blessing Fubara
(74) Attorney, Agent, or Firm—Keil & Weinkauf

(57) ABSTRACT

A fast-acting analgesic comprises as analgesic substance ibuprofen in an adjuvant matrix with a porous structure and a density of greater than 1 and up to 2.5 g/cm$^3$.

10 Claims, 1 Drawing Sheet

FAST-ACTING ANALGESIC

The present invention relates to a fast-acting analgesic preparation comprising as analgesic substance ibuprofen in an adjuvant matrix, where the preparation has a porous structure and a density of greater than 1 and up to 2.5 g/cm$^3$.

The invention furthermore relates to a process for producing the preparation.

The use of ibuprofen, 2-(4-isobutylphenyl)propionic acid, as nonsteroidal analgesic has been known for a relatively long time. Ibuprofen has an asymmetric carbon atom and, in the form used therapeutically, is generally in the form of the racemate.

The low solubility of the active substance is a problem with regard to the rapid onset of action which is required in the treatment of pain.

DE-C 36 39 038 discloses the achievement of a faster onset of action by using the pure S(+) isomer.

DE-C 41 40 185 proposes solving the problem of the low solubility of ibuprofen by using colloidal dispersion systems based on gelatin.

The problem of low solubility is furthermore frequently solved by converting ibuprofen into its water-soluble salts. However, sodium ibuprofenate, for example, is hygroscopic and can be tableted only poorly.

Ibuprofen is also available as lysine salt which, compared with the free acid, achieves a distinctly faster and higher maximum blood level $C_{max}$ and is currently regarded as the fastest dosage form. However, the conversion of the acid into the salt is more elaborate and more costly. In addition, lysine has, as amino acid, an allergenic potential, which is why the lysine salt has not been approved as medicinal product in some countries.

WO 96/29061 describes the production of transparent solid solutions of ibuprofen salts by a melt extrusion process.

It is an object of the present invention to find a fast-acting preparation of ibuprofen which achieves an effect which is as good as that of the lysine salt.

We have found that this object is achieved by the preparation defined at the outset, and a process for producing it.

Ibuprofen is processed according to the invention as free acid, preferably in the form of the racemate. However, it is also possible to use S(+)-ibuprofen. Depending on the dosage, the preparations may comprise from 5 to 80, preferably from 20 to 60, % by weight of ibuprofen. Suitable dosages are, for example, 200 mg or 400 mg per drug form. The active ingredient is preferably in the form of solid solution in an adjuvant matrix. The term "solid solution" is known to the skilled worker (cf. Chiou and Riegelmann, J. Pharm. Sci. 60(9), (1971) 1281–1301).

Besides water-soluble polymeric binders, the adjuvant matrix comprises carbonates and, where appropriate, conventional pharmaceutical adjuvants. Water-soluble means that at least 0.5 g, preferably at least 2 g of the polymer dissolve, where appropriate colloidally, in 100 g of water at 20° C.

Suitable polymeric binders according to the invention are water-soluble cellulose derivatives such as hydroxyalkylcelluloses, for example hydroxypropylcellulose, and, in particular, water-soluble homo- and copolymers of N-vinylpyrrolidone (NVP) with K values in the range from 10 to 90, preferably K25 to K30. Examples of suitable copolymers are copolymers of NVP and vinyl acetate, for example a copolymer of 60% by weight NVP and 40% by weight vinyl acetate with a K value of 28 or 30. Polyvinylpyrrolidone (PVP) with a K value of 30 is particularly preferred as polymeric binder (for determination of the K value, see H. Fikentscher, Cellulosechemie 13 (1932) 58–64 and 71–74). It is also possible to employ mixtures of binders. The polymeric binders can be employed in amounts of from 10 to 80, preferably 30 to 70, % of the total weight of the preparation.

Suitable carbonates according to the invention are the alkali metal carbonates sodium carbonate and potassium carbonate, and the alkaline earth metal carbonates calcium carbonate and magnesium carbonate. Also suitable furthermore are the corresponding bicarbonates of sodium and potassium.

The carbonates or bicarbonates can be employed in amounts of from 0.1 to 20, preferably 2 to 15, % of the total weight of the preparation. Anhydrous carbonates or bicarbonates are preferably employed. It is also particularly preferred to employ ground carbonates, in which case the particle sizes are preferably less than 500 µm.

The preparations may additionally also contain conventional pharmaceutical adjuvants in the amounts customary for this purpose, for example stabilizers, antioxidants, dyes, flavorings, bulking agents or stabilizers such as highly disperse silica or lubricants. The drug forms may furthermore also comprise codeine, caffeine or vitamin C in the amounts customary for this purpose.

The preparations according to the invention are produced by mixing the components using shear forces and supplying thermal energy. The mixing preferably takes place in a single-screw or multiscrew extruder, particularly preferably a twin-screw extruder. The supply of thermal energy produces a melt of the mixing components. This normally takes place by heating the extruder jacket to from 50 to 180, preferably 80 to 130° C. The active ingredient can be mixed with the other components before or after the melting of the polymeric binder. The melts are solvent-free. This means that no water or organic solvents are added.

The molten mixture of the components is conveyed by the screw movement toward the extruder outlet, which preferably consists of a die. The pressure is reduced to from 10 to 600 mbar, preferably 30 to 200 mbar, particularly preferably 50 to 150 mbar, according to the invention in the last segment or section before the die. After extrusion through the die, the still plastic composition is shaped to suitable drug forms.

Suitable drug forms are preferably tablets, for example bolus tablets, lenticular tablets or else buccal tablets, pastilles, instant granules, granules or pellets for sachets or for filling capsules. Suppositories are also suitable according to the invention.

Tablets are preferably produced by the process described in EP-A 240 906 by passing the still plastic extrudate between two rolls which are driven in opposite directions and have mutually facing depressions in the surface of the rolls. It is also possible to obtain tablets with scores by appropriate choice of the shape of these depressions. Granules or pellets can be obtained by cold cutting or, preferably, by hot cutting.

The drug forms may additionally be provided with coatings known per se which have no effect on the release behavior.

The drug forms according to the invention are suitable for the preferred oral administration. They have a density, determined using a helium pycnometer, of more than 1 and up to 2.5, preferably from 1.1 to 2.0, particularly preferably from 1.4 to 1.9, g/cm$^3$ and are porous. The density is determined using a helium pycnometer in accordance with OECD Guideline, Paris 1981, Test Guideline, page 100, or according to DIN 55990 or DIN 53243. This entails determination of the volume of liquid helium displaced. In contrast to conventional methods, this procedure provides the true density of a solid and not the apparent density. The helium is able, because of its small atomic diameter, to penetrate into the smallest fissures and pores.

The average pore size is preferably 80 $\mu$m, and the pores may have diameters of from 10 to 300 $\mu$m. A honeycomb-like structure is evident in the cross section through a drug form.

The active ingredient is particularly preferably present as solid solution in the matrix, which can be demonstrated by DSC measurements (Differential Scanning Calorimetry) and by X-ray diffraction investigations. The drug forms may, however, also be present as mixed forms in which part of the active ingredient is in the form of a solid solution and another part is recrystallized. The active ingredient can also be in completely recrystallized form. The proportion of recrystallized free acid can be controlled by the amount of carbonate added.

In contrast to known solid solutions of ibuprofen, the drug forms according to the invention are, however, not transparent but have an opaque appearance.

The release rate for the active ingredient by the USP23 rotating basket method is at least 95% after 10 min.

The preparations according to the invention show not only rapid release but also a rapid action. The time ($t_{max}$) until the maximum blood plasma level ($C_{max}$) is reached is in the region of 0.5 hour.

The AUCs (areas under the concentration-time curves), which are a measure of the amount of substance in the body, for the drug forms according to the invention are substantially comparable with those for a commercial fast-acting ibuprofen lysinate.

In view of the prior art, it was completely surprising that the drug forms according to the invention are bioequivalent to the lysinates.

It was also surprising that porous forms with a density of greater than 1 g/cm$^3$ were obtained by reducing the pressure before the extruder outlet.

EXAMPLES

Figure 1:
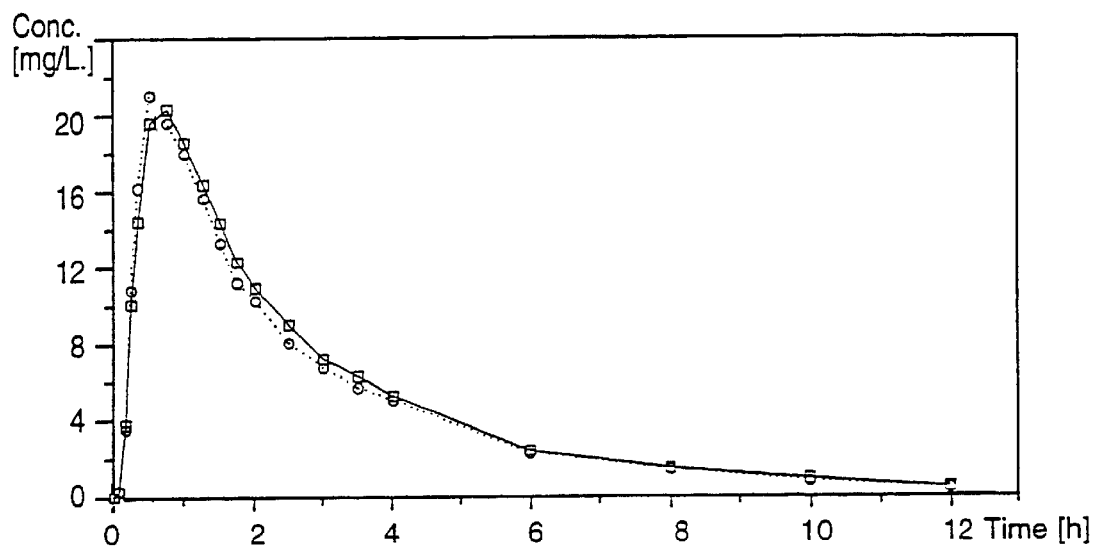
FIG. 1 is a graph plotting blood plasma concentration over time.

The compositions indicated in each of the following examples were premixed and introduced into the feed section of a twin-screw extruder (ZSK-40, Werner & Pfleiderer). Extrusion took place with a product throughput of 25 kg per hour at a screw speed of 90 rpm. The temperatures in the individual zones (sections) of the extruder and the heated die strip were:

section 1: 80° C., section 2: 120° C., section 3: 130° C., section 4: 130° C., head: 130° C., die 130° C. The pressure in section 4 was 51.5 mbar. Bolus tablets were produced from the extrudate by the calendering process described in EP-A 240 906.

The release of active ingredient was measured by the USPXXIII basket method. Determination takes place at 37° C. in a no-change test at a pH of 7.2 and at 150 rpm. The test medium employed was a 0.05 molar aqueous potassium dihydrogen phosphate solution which had been adjusted to pH 7.2 with sodium hydroxide solution. An appropriate amount of drug form was weighed out. The assay was carried out photometrically by means of a derivative spectrum at 256 to 270 nm with external standard calibration.

The tablets were provided with a commercially obtainable coating (Opadry® OY-S-24939 supplied by Colorcon), a 15% strength by weight aqueous dispersion of the following composition: 58.04% hydroxypropylmethylcellulose (HPMC) with a viscosity of 6 mPas, 5.76% HPMC with a viscosity of 15 mPas, 5.76% hydroxypropylcellulose, 11.16% talc, 9% polyethylene glycol (PEG) 400, 1.61% PEG 6000, 8.18% titanium dioxide, 0.19% red iron oxide, 0.15% highly disperse silica, 0.15% sodium docusate (% in each case % by weight). Coating took place in a known manner by spraying in a coating pan.

The density was determined in liquid helium using an ultrapycnometer 1000 supplied by Quantachrome Corp.

EXAMPLE 1

| | |
|---|---|
| PVP K 30 | 55.07% by weight |
| Copolyvidone* K28 | 10.89% by weight |
| Na$_2$CO$_3$ anhydrous (DAB) | 10.00% by weight |
| Ibuprofen | 23.53% by weight |
| Highly disperse silica | 0.51% by weight |

(*Copolymer of 60% by weight vinylpyrrolidone and 40% by weight vinyl acetate)

Tablet weight: 850 mg without coating, coating 15 mg,
Ibuprofen dose 200 mg,
Release after 10 min 100%
Density of the uncoated tablet core 1.573 g/cm$^3$

EXAMPLE 2

| | |
|---|---|
| PVP K 30 | 55.50% by weight |
| Na$_2$CO$_3$, anhydrous | 12.00% by weight |
| Ibuprofen | 32.00% by weight |
| Highly disperse silica | 0.5% by weight |

Tablet weight: 650 mg, coating 15 mg,
Ibuprofen dose 200 mg
Release after 10 min 100%
Density of the uncoated tablet core 1.841 g/cm$^3$

EXAMPLE 3

| | |
|---|---|
| PVP K30 | 41.00% by weight |
| Na$_2$CO$_3$ anhydrous | 12.00% by weight |
| Ibuprofen | 47.00% by weight |

Tablet weight: 850 mg without coating
Ibuprofen dose 400 mg
Determination of the Pharmacokinetic Parameters The study was carried out with a single dose (200 mg) with triple crossover on healthy men.

A drug form from Example 1 was administered. For comparison, a commercially obtainable ibuprofen lysinate (Dolormin® film-coated tablets, 342 mg of ibuprofen D,L-lysine salt, equivalent to 200 mg of ibuprofen) was administered.

TABLE

| Pharmacokinetic parameters | Example 1 | Dolormin |
| --- | --- | --- |
| AUC [mg*h/L] | 62.78 | 57.41 |
| $C_{max}$ [mg/L] | 22.77 | 23.19 |
| $AUC_{0-1h}$ [mg*h/L] | 15.23 | 15.55 |
| $t_{max}$ [h] | 0.50 | 0.50 |

The geometric mean is indicated in each case (n=12).

FIG. 1 depicts the blood plasma plot over a period of 12 hours. This is a plot of the plasma concentration [mg/L] against the time [h] as geometric mean, n=12.

-□- Ibuprofen 200 mg film-coated tablet of Example 1

... O ... Dolormin film-coated tablet

There is very substantial identity of the plots.

In addition, the fracture surface of an uncoated tablet of Example 1 was examined under the electron microscope. A metal-coated fracture surface was examined.

There were pores open to the fracture surface. Closed pores were also evident as small circular depressions.

We claim:

1. A fast-acting analgesic drug form having a release rate of active ingredient of at least 95% after 10 minutes (USP 23) comprising as analgesic substance ibuprofen in an adjuvant matrix, having a porous structure and a density of greater than 1 and up to 2.5 g/cm³.

2. An analgesic as claimed in claim 1, having a density of from 1.4 to 1.9 g/cm³.

3. An analgesic as claimed in claim 1, comprising as matrix adjuvant at least one melt-processable polymeric binder.

4. An analgesic as claimed in claim 3, comprising as polymeric binder a homo- or copolymer of N-vinylpyrrolidone.

5. An analgesic as claimed in claim 1, obtainable by application of shear forces and extrusion of a mixture of ibuprofen and the matrix adjuvants.

6. An analgesic as claimed in claim 1, obtainable by use of alkali metal or alkaline earth metal carbonates as matrix adjuvants.

7. An analgesic as claimed in claim 1, comprising ibuprofen as racemate.

8. A process for producing an analgesic as claimed in claim 1, by mixing the analgesic substance with the matrix adjuvants with application of shear forces and extrusion through a die with subsequent shaping, wherein the plasticized mixture is exposed to a vacuum before extrusion through the die.

9. An analgesic as claimed in claim 1 having pore diameters of from 10 to 300 μm.

10. An analgesic as claimed in claim 9 having an average pore diameter of 80 μm.

* * * * *